(12) United States Patent
Mayne-L'Hermite et al.

(10) Patent No.: US 10,106,403 B2
(45) Date of Patent: Oct. 23, 2018

(54) CHEMICAL SENSORS CONTAINING CARBON NANOTUBES, METHOD FOR MAKING SAME, AND USES THEROF

(75) Inventors: Martine Mayne-L'Hermite, Les Molieres (FR); Serge Palacin, Montigny le Bretonneux (FR); Pascale Chenevier, Villebon sur Yvette (FR); Jérôme Chancolon, Mardie (FR); Aurélien Gohier, Antony (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 286 days.

(21) Appl. No.: 13/121,377

(22) PCT Filed: Sep. 28, 2009

(86) PCT No.: PCT/EP2009/062562
§ 371 (c)(1),
(2), (4) Date: Jun. 17, 2011

(87) PCT Pub. No.: WO2010/034840
PCT Pub. Date: Apr. 1, 2010

(65) Prior Publication Data
US 2011/0244585 A1    Oct. 6, 2011

(30) Foreign Application Priority Data

Sep. 29, 2008    (FR) ...................................... 08 56519

(51) Int. Cl.
*B82Y 30/00*    (2011.01)
*B82Y 15/00*    (2011.01)

(52) U.S. Cl.
CPC ............... *B82Y 30/00* (2013.01); *B82Y 15/00* (2013.01); *Y10T 436/142222* (2015.01);
(Continued)

(58) Field of Classification Search
CPC ................... B82Y 30/00; B82Y 15/00; Y10T 436/204998; Y10T 436/205831;
(Continued)

(56) References Cited

U.S. PATENT DOCUMENTS 7,312,095 B1    12/2007 Gabriel et al.
7,318,908 B1    1/2008  Dai
(Continued)

FOREIGN PATENT DOCUMENTS

EP    1884770    2/2008
WO    WO 2004/000727    12/2003
(Continued)

OTHER PUBLICATIONS

Cambaz, Z. Goknur, Noncatalytic synthesis of carbon nanotubes, graphene and graphite on SiC, Carbon, May 6, 2008, 46, pp. 841-849.*

(Continued)

*Primary Examiner* — Christine T Mui
(74) *Attorney, Agent, or Firm* — Knobbe Martens Olson & Bear LLP

(57) ABSTRACT

A device is disclosed for detecting at least one chemical compound comprising at least one carbon nanotube with several graphene layers, on which is grafted at least one molecule bearing group G1 capable of reacting with the chemical compound or a precursor of such a group G1. The uses and the method of making such a device is also disclosed.

22 Claims, 5 Drawing Sheets

(52) U.S. Cl.
CPC .... *Y10T 436/16* (2015.01); *Y10T 436/163333* (2015.01); *Y10T 436/172307* (2015.01); *Y10T 436/175383* (2015.01); *Y10T 436/18* (2015.01); *Y10T 436/19* (2015.01); *Y10T 436/204998* (2015.01); *Y10T 436/205831* (2015.01); *Y10T 436/214* (2015.01); *Y10T 436/22* (2015.01)

(58) Field of Classification Search
CPC . Y10T 436/172307; Y10T 436/163333; Y10T 436/175383; Y10T 436/142222; Y10T 436/22; Y10T 436/18; Y10T 436/19; Y10T 436/16
USPC ......... 436/96, 144, 143, 104, 119, 103, 141; 422/500; 977/742, 745, 957, 842, 953, 977/932, 840
See application file for complete search history.

(56) References Cited

U.S. PATENT DOCUMENTS

| | | |
|---|---|---|
| 2002/0117659 A1 | 8/2002 | Lieber et al. |
| 2006/0263255 A1 | 11/2006 | Han et al. |
| 2007/0145359 A1 | 6/2007 | Che |

FOREIGN PATENT DOCUMENTS

| | | |
|---|---|---|
| WO | WO 2005/026694 | 3/2005 |
| WO | WO 2005/031299 | 4/2005 |
| WO | WO 2005/033378 | 4/2005 |
| WO | WO 2005/062031 | 7/2005 |
| WO | WO 2006/097611 | 9/2006 |
| WO | WO 2008/078052 | 7/2008 |

OTHER PUBLICATIONS

Bahr et al, Highly functionalized carbon nanotubes using in situ generated diazonium, Chem. Mater. vol. 13, pp. 3823-3824, 2001.
Banet et al, Efficient probes for fast detection of chlorine gas at ppb level, Sensors & Transducers Journal, vol. 83, Issue 9, pp. 1541-1548, Sep. 2007.
Bender et al, Characterization of a WO3 thin film chlorine sensor, Sensors and Actuators B, vol. 77, pp. 281-286, 2001.
Bittencourt et al, WO3 films modified with functionalized multi-wall carbon nanotubes: Morphological, compositional and gas response studies, Sensors and Actuators B, vol. 115, pp. 33-41, 2006.
Jang et al, A simple approach in fabricating chemical sensor using laterally grown multi-walled carbon nanotubes, Sensors and Actuators B, vol. 99, pp. 118-122, 2004.
Kong et al, Nanotube molecular wires as chemical sensors, Science, vol. 287, pp. 622-625, Jan. 28, 2000.
Li et al, Nano chemical sensors with polymer-coated nanotubes, IEEE Sensors Journal, vol. 6, No. 5, pp. 1047-1051, Oct. 2006.
Niizeki et al, Room temperature operating solid-state sensor for chlorine gas, J. Electrochem. Soc., vol. 145, No. 7, Jul. 1998.
Qi et al, Toward large arrays of multiplex functionalized carbon nanotube sensors for highly sensitive and selective molecular detection, Nano Letter vol. 3, No. 3, pp. 347-351, Feb. 6, 2003.
Roy et al, Room temperature sensor based on carbon nanotubes and nanofibres for methane detection, Vacuum, vol. 77, pp. 223-229, 2005.
Suehiro et al, Fabrication of a carbon nanotube-based gas sensor using dielectophoresis and its application for ammonia detection by impedance spectroscopy, Journal of Physics D: Applied Physics, vol. 36, pp. L109-L114, 2003.
Valentini et al, Sensors for sub-ppm NO2 gas detection based on carbon nanotube thin films, Applied Physics Letters, vol. 82, No. 6, pp. 961-963, Feb. 10, 2003.
Wang et al, Multi-walled carbon nanotube-based gas sensors for NH3 detection, Diamond and Related Materials, vol. 13, pp. 1327-1332, 2004.
Wei et al, A novel SnO2 gas sensor doped with carbon nanotubes operating at room temperature, Sensors and Actuators B, vol. 101, pp. 81-89, May 5, 2004.
International Search Report dated Dec. 29, 2009 for PCT/EP2009/062562.
Horváth, et al. 2008. The role of defects in chemical sensing properties of carbon nanotube films. *Applied Physics A*, 93:495-504.
Penza, et al. 2007. Effect of growth catalysts on gas sensitivity in carbon nanotube film based chemiresistive sensors. *Applied Physics Letters*, 90:103101-1-103101-3.
Pinault et al. 2004. Carbon nanotubes produced by aerosol pyrolysis: Growth mechanisms and post-annealing effects. *Diamond and Related Materials*, 13:1266-1269.

\* cited by examiner

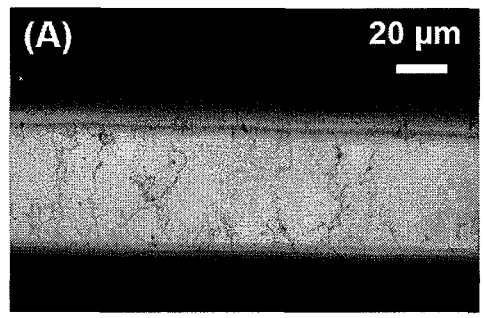
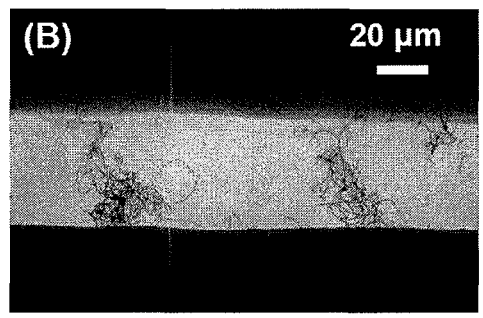
FIG.3A  FIG.3B
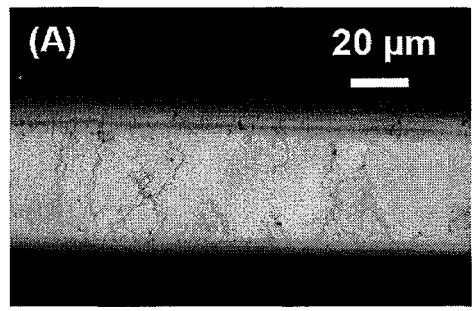
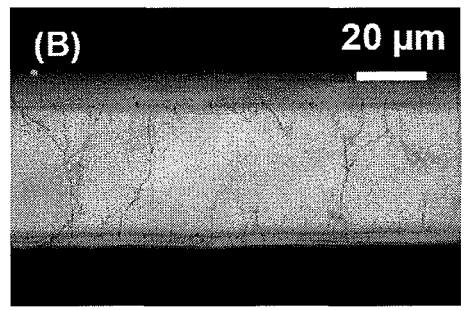
FIG.4A  FIG.4B
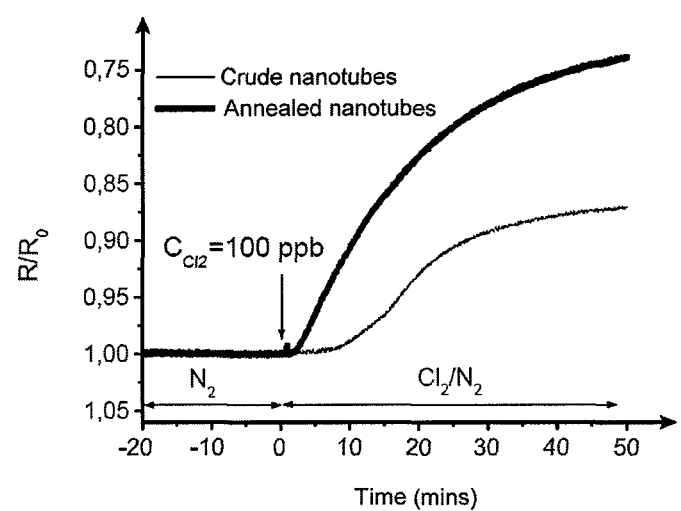
FIG.5

CHEMICAL SENSORS CONTAINING CARBON NANOTUBES, METHOD FOR MAKING SAME, AND USES THEROF

TECHNICAL FIELD

The present invention relates to the field of detection, identification and quantification of gaseous chemical species and notably toxic gaseous chemical species.

The present invention more particularly relates to a device of the chemical sensor type comprising functionalized multisheet carbon nanotubes and allowing such a detection, identification and quantification, to its preparation method and to its uses. The functionalization appears as a fine layer of polymer or else as a few chemical groups at the surface of the carbon nanotubes.

BACKGROUND

Detection of toxic chemical substances in the atmosphere is an important guarantee of our safety both in civilian or professional life. Limiting average exposure values are moreover already established for a great number of chemical agents. In this background, development of performing chemical sensors, i.e. which transform chemical information into a useful analytic signal, is therefore an absolute necessity.

However, strong constraints restrict the manufacturing of such chemical sensors, the latter having to be both sensitive and selective.

Indeed, the sensor should be very sensitive to the target chemical agent, i.e. be capable of delivering a response for contents below the limiting contents (ppm or ppb depending on the gases).

The sensor should also be selective, i.e. it should be able to distinguish between several chemical agents.

To these fundamental constraints, other more secondary issues may be added to the specifications sheet.

Thus, it is preferable that
the sensor have low bulkiness, in other words it may be miniaturizable, in order to carry out analysis directly in the medium to be analyzed instead of proceeding with sampling;
the sensor should be simple to manufacture in order to have a production cost as low as possible;
the sensor during operation should consume little energy and this for increased portability;
that the sensor may be used several times (reversibility principle of the sensor).

Many toxic gases are targeted by devices of the sensor type: volatile organic compounds, ammonia, nitrogen oxide, chlorinated compounds, dimethyl methylphosphonate (DMMP), hydrogen, methane . . . . The state of the art on sensors of chemical agents presented hereafter more particularly relates to the devices allowing detection of chlorine gas and sensors based on carbon nanotubes.

The chlorine concentration value which may cause an immediate hazard for life and health is about 10 ppm. The limiting weighted average exposure of chlorine (8 hrs of exposure per working day) has been evaluated as 500 ppb for certain public bodies such as the Commission de la Sante et de la Sécurité du Travail (Occupational Health and Safety Commission) (Canadian Organization). This is why it is required to ensure detection of this gas at concentrations of the order of hundreds of ppb, or even below.

Generally, sensors of chemical agents consist of two main components: a recognition system and a signal transducer. They are classified according to their transduction method: electric, calorimetric, electrochemical, optical, mass or magnetic transduction and affect four different types of markets which are the health, environment, industry and defense markets.

Different chlorine-sensitive sensors already exist: mention may be made of potentiometric sensors, ionization sensors, optochemical sensors and resistive sensors from semiconducting materials.

Potentiometric sensors are based on making a solid electrolyte, for example $SrCl_2$—KCl or $PbCl_2$—KCl or $BaCl_2$KCl. The operating principle of these sensors is based on the measurement of a potential, which varies depending on the chlorine content. Typically, the responses of these sensors are studied for ranges of concentrations above 1 ppm. The main drawback of this type of sensor is therefore their low sensitivity. Moreover even if detection is reported to be at room temperature in certain studies [1], the system is generally heated to a temperature typically above 300° C.

The principle of ionization sensors consists of ionizing chlorine when the latter passes close to a source of electrons (thermo-ionic emission). The chlorine content may be estimated from the collected current. With this technique, it is possible to detect very low chlorine contents, below 100 ppb, independently of temperature and humidity. The drawback of this method however is the non-portability of the measurement method, preventing a measurement in situ.

The principle of optochemical sensors is based on the study of optical properties of thin films sensitive to the gas to be detected, these films may be sensitive to a single gas in particular (principle of the selective sensor). The adsorption or the reaction of the gas at the sensitive film leads to an effective change in its fluorescence or absorbance properties, at specific wavelengths. With the rate of change of the absorbance or of the fluorescence, it is possible to trace back the concentration of the studied chemical agent. In the specific case of chlorine, the shaped sensitive films may be phenylporphyrin, o-toluidine, tris-bipyridyl ruthenium complexes or else nanoporous films containing specific molecules or ions ($Br^-$, $I^-$) [2]. With these opto-chemical devices, it is possible to detect chlorine at a low content, down to 50 ppb [2]. Moreover, let us note that the detection occurs at room temperature. The drawback of this type of sensor is the manufacturing cost of a complete device which notably comprises the sensitive film, a diode and a detector.

For resistive sensors from semiconductors, it is the measurement of the resistance of the device which allows detection of the gaseous agents. This is the type of chemical sensor which is most frequently encountered in the literature, notably for detecting chlorine. The adsorption of a gas at the surface of the semiconductor may induce a charge transfer which leads to the generation of carriers and to a modification in the conductivity of the system. The sensitive layers may be organic semi-conductors such as metal phthalocyanin or else metal oxide semiconductors such as $InO_2$, $WO_2$ or $SnO_2$. Detectors based on semiconductors are devices which are very sensitive to chlorine. The literature reports devices having very low detection thresholds: from 50 ppb [3]. However, let us note that the detection only becomes effective when these sensors are heated, typically at temperatures above 150° C. The fact that they do not operate at room temperature is their main flaw. Moreover, it is noted that in the specific case of chlorine the selectivity of this type of sensor is never mentioned.

To summarize, among the different devices described above, none of them totally meets the criteria established earlier.

Since a few years, a novel very promising material, the carbon nanotube, has been used in many studies, as the sensitive component in chemical sensors.

The devices based on carbon nanotubes benefit from the singular properties of this material. Firstly, the carbon nanotubes have a very large specific surface area, which may attain 1,500 m$^2$/g and which thereby provides a very large surface for interaction with the surrounding atmosphere. Secondly, carbon nanotubes have a very high electric conductivity which proves to be extremely sensitive to the adsorption of molecules on their surface, and therefore more generally to their environment. The combination of these properties makes a carbon nanotube a very interesting material as a sensitive component in chemical sensors. Further, the small size of the carbon nanotubes is favorable for making miniaturized devices.

Many types of chemical sensors based on nanotubes are listed in the literature. These may be sensors based on the CNTFET (Carbon NanoTube Field Effect Transistor) principle, sensors of the resistive type based on the measurement of the resistance of the system, acoustic sensors, sensors for measuring impedance, ionization sensors . . . . Only the sensors of the CNTFET type and of the resistive type based on carbon nanotubes will be explained hereafter, both types being the closest to the present invention.

A first approach consists of dispersing (single-walled or multi-walled) carbon nanotubes in a sensitive array. The operating principle is the same as that of the resistive semiconductor sensors (measurement of the change in resistance of the system). The studied matrices are either tin oxide ($SnO_2$), or polymers (PMMA, polystyrene) or further tungsten oxide ($WO_3$) [4,5]. The gases detected by these devices are nitrogen dioxide ($NO_2$), tetrahydrofurane (THF), chloromethanes and other volatile organic compounds (VOCs). By comparing the devices with a control (without any nanotube), it appears that sensors including nanotubes are much more competitive, notably in terms of sensitivity [4]. The detection thresholds observed at room temperature may at best be less than 1 ppm (500 ppb for $NO_2$ in reference [5]).

Another approach is interested in direct synthesis of carbon nanotubes within the «sensor» device. The principle of this type of sensor is shown in patent application US 2007/0145356 [6]; however no detection example by means of such a device is shown in this document. In this type of device, the growth may be controlled so as to obtain a unique single-sheet carbon nanotube providing the junction between two metal electrodes, deposited by lithography. The silicon substrate, which may be biased, acts as a grid. First studies, carried out in 2000 by Kong et al. on these devices measure the conductance of the nanotube at room temperature versus the gas environment [7]. The observed detection limits are 2 ppm for $NO_2$, and 0.1% for $NH_3$. By using the same type of device, but this time with carbon nanotubes covered with a thin layer of polyethyleneimine, Qi et al. were able to reduce the $NO_2$ sensitivity threshold to 100 ppt [8].

Multi-walled nanotubes may also be used as a sensitive component directly synthesized within the device. In the same way, as in the previous paragraph, multi-walled nanotubes may be synthesized laterally and with a low density between two electrodes [9]. These sensors, notably sensitive to ammonia, have a detection threshold of 50 ppm [9]. In most of the devices, the elaboration of which comprises a phase for synthesis of multi-walled nanotubes, the growth of the nanotubes is massive and is directly carried out on a substrate (Si, $SiO_2$ or $Si_3N_4$) from a thin catalyst layer (a few nanometers). Measurement of the resistance of the system is carried out by means of interdigitated electrodes deposited beforehand (under the catalyst layer) or else by depositing two metal electrodes over the film formed by the nanotubes. This type of sensors may be heated in order to improve the detection performances. In the example shown in reference [10], the device operates at a temperature of 165° C. and exhibits a very low detection threshold of about 10 ppb for nitrogen dioxide. Other gases studied by means of the same sensor, ethanol and benzene, as for them, have much higher detection thresholds (>>1 ppm). The detection thresholds for methane ($CH_4$) and for hydrogen ($H_2$) measured by other groups with the same type of device are also very high (>1,000 ppm). Among the devices shown in this paragraph, only the sensor sensitive to methane is investigated at room temperature [11].

A third approach with several steps consists of carrying out in a first phase, the synthesis of the carbon nanotubes, and then of dispersing them in a solvent, and finally depositing the nanotubes from the dispersion obtained beforehand on a network of lithographed electrodes, the evolution of the resistance between the electrodes then allowing detection of the pollutants targeted by the study. A device consisting of single-walled nanotube aggregates achieving the connection between interdigitated electrodes was also developed. With this device which operates at room temperature and in which the nanotubes are covered with a layer of chlorosulfonated polyethylene polymer, the observed chlorine detection threshold remains rather high: >2 ppm [12].

The multi-walled nanotubes may also be dispersed and then deposited randomly on electrodes [13]. With such a device (with two electrodes), Wang et al. report detection of ammonia at room temperature from 5 ppm onwards.

Let us note that in this third approach, the carbon nanotubes deposited on the electrodes during the shaping of the sensor are oriented randomly. A few investigations use the dielectrophoresis technique for aligning the nanotubes in a preferential way perpendicularly to the electrodes. The dielectrophoresis technique consists of applying an alternating electric field between the electrodes. By using this deposition method for multi-walled carbon nanotubes, Suehiro et al. made a device with which ammonia was able to be detected from 500 ppb onwards at room temperature [14].

A few patent documents have chemical sensors based on the measurement of the conduction of single-sheet carbon nanotubes, the nanotubes being individual or organized as networks between lithographed electrodes [15-17]. In these documents, a sensitive layer is added to the nanotube(s) connected to the electrodes. Patent application US 2006/0263255 reports the use of single-walled nanotubes covered with palladium particles for detecting hydrogen [17]. International applications WO 2005/026694 and WO 2005/062031 show $CO_2$-sensitive devices based on single-walled carbon nanotubes covered with a layer of polyethyleneimine [15,16]. The polymer is deposited by simply adding a drop of solution onto the device. Other functionalizing agents are shown in these patents (metal carbonates, aromatic compounds, various amine compounds . . . ) but no example is associated with them. It is important to note that the functionalizing agents are deposited by impregnation (physical absorption) and are not grafted to the nanotube in a covalent way. U.S. Pat. No. 7,312,095 proposes functionalization of single-sheet nanotube(s) integrated into a sensor device by causing a strong current to flow in the latter while exposing it to a reagent assumed to be sensitive to a specific gas [18]. However no example is shown in the latter patent.

The design of a device meeting the whole of the constraints listed earlier still remains presently a challenge which is only partly faced. The manufacturing of such a sensor therefore is a very important issue.

DESCRIPTION OF CERTAIN INVENTIVE ASPECTS

According to some aspects a device is disclosed of the chemical sensor type which meets the needs and technical problems mentioned earlier, i.e. a device sensitive to chemical agents notably to optionally toxic, gaseous chemical agents. The device according to some aspects is in particular distinguished by the fact that it is selective and highly sensitive, even at room temperature. It is therefore not absolutely necessary to add a heating system to it, which is costly in terms of energy. Moreover, the device according to some aspects is simple to form.

Thus, the whole of the technical problems solved by the present invention are the following:
- the variable or even low sensitivity of the sensors of the prior art;
- the non-selectivity of sensors of the prior art with regard to a given gas;
- the bulkiness of the sensors of the prior art only allowing detection by sampling and not detection in situ;
- the requirement of heating the sensors of the prior art of the «resistive sensors» type for detecting chemical agents;
- the use of costly lithographic techniques to be applied for manufacturing sensors of the prior art based on carbon nanotubes.

Further, the device according to the invention is remarkable since it may be used not only for detecting chlorine but also any gas chemical compound whether the latter is toxic or not.

The present invention therefore relates to a device intended to detect at least one chemical compound, comprising at least one carbon nanotube with several layers of graphene, on which is grafted at least one molecule bearing a group $G_1$ capable of reacting with said chemical compound or a precursor of such a group $G_1$.

Advantageously, the device according to the present invention comprises at least 2 nanotubes; notably at least 10 nanotubes; in particular, at least 50 nanotubes; more particularly, at least 100 nanotubes and, most particularly, at least 200 carbon nanotubes with several layers of graphene, each nanotube being grafted with at least one molecule and preferably several molecules bearing a group $G_1$ capable of reacting with said chemical compound or a precursor of such a group $G_1$. By «several molecules», are meant within the scope of the present invention, at least 5, notably at least 10, in particular at least 50 and most particularly at least 100 molecules.

The carbon nanotubes applied within the scope of the present invention are nanotubes with several graphene layers. These nanotubes are also known under the designations: multi-walled nanotubes, multi-sheet nanotubes or MWNT for «Multi-Walled Nanotubes». As an interesting and remarkable fact, the use of nanotubes with several functionalized graphene layers, i.e. nanotubes, the surface of which has been modified in a covalent way, does not compromise their conduction properties unlike single-sheet carbon nanotubes.

One skilled in the art is aware of various techniques with which such carbon nanotubes may be prepared. As examples, mention may be made of the chemical method consisting of pyrolysis of carbon sources on metal catalysts and being similar to the CVD method such as notably the pyrolysis method, object of international application WO 2004/000727 [19]. This method is based on the catalytic breakdown of a mixed liquid aerosol generated from a solution of ferrocene dissolved in toluene (5 wt %). An ultrasonic aerosol generator (Pyrosol 7901, RBI Company, France) or an injector (for example of the automotive injector type) may be used. Argon, used as a carrier gas (1 L/min), carries away the aerosol at a quartz reactor heated to 850° C. Aligned nanotubes with several layers of graphene with a length of a few hundred micrometers, having a diameter comprised between ten and a hundred nanometers are harvested on the walls of the reactor after the synthesis.

The carbon nanotubes which the device according to the invention comprises, are long nanotubes: they have a length comprised between 1 μm and 1 mm, notably between 10 μm and 800 μm, in particular between 15 μm and 600 μm and, most particularly greater than or equal to 20 μm. The diameter of these nanotubes is comprised between 2 and 150 nm, notably between 5 and 130 nm and, in particular between 10 and 100 nm.

Finally, the carbon nanotubes which the device according to the present invention comprises are advantageously annealed nanotubes. By «annealed nanotubes», are meant, within the scope of the present invention, carbon nanotubes which, once prepared, are subject under an inert atmosphere to a temperature above 800° C., notably above 1,000° C., in particular above 1,500° C. and more particularly to a temperature of about 2,000° C. (i.e. 2,000° C.±200° C.) for several hours. By «several hours» are meant within the scope of the present invention at least 1, notably at least 6, notably in particular at least 12 and most particularly at least 18 hours. These conditions are notably those applied during step (a) of the method hereafter. With this annealing advantageously carried out in an oven, it is possible to obtain nanotubes free of any synthesis byproducts such as catalytic materials based on iron and better crystallised since they have a larger long-range structural order. Sensors based on annealed nanotubes have a very good structural property, which allows improvement of their sensitivity as compared with crude nanotubes, i.e. nanotubes not having been subject to annealing (see the examples hereafter).

The invention occupies an original place with respect to the different devices of the sensor type, notably those based on carbon nanotubes. It is based on the use of long nanotubes with several graphene layers as a sensitive component in the device. On the other hand, the invention benefits from the carbon nanotubes capability of being functionalized, i.e. of being modified at their surface by covalent grafting of chemical functions or of polymer chains. The proposed device therefore integrates functionalized carbon nanotubes with several layers of graphene, having affinity with the targeted gas. With this innovative aspect of the device, selectivity may be guaranteed.

It should be noted that the chemical modification of the surface of the carbon nanotubes by grafting in a covalent way a molecule bearing a group $G_1$ capable of reacting with said chemical compound or a precursor of such a group $G_1$ for selected detection of said compound is an approach which is different from the devices of the prior art [12], in which a polymer layer is deposited on the whole of the sensor device, after elaboration of the nanotube/electrodes system.

By «molecule bearing a group $G_1$ capable of reacting with said chemical compound», is meant any natural or synthetic molecule, advantageously an organic molecule comprising from a few atoms to several tens or even hundreds of atoms. This molecule may therefore be a chemical function, a simple molecule or a molecule having a more complex structure such as a polymer structure. Regardless of the structure of this molecule, the essential features within the scope of the present invention are the fact that:

on the one hand, the molecule is bound to the implemented carbon nanotube in a covalent way, by means of a bond involving an atom of said molecule and an atom of said carbon nanotube, said molecule therefore comprises a function involved in the covalent bond with the surface of the nanotube;

on the other hand, the molecule comprises a group $G_1$ capable of reacting with said chemical compound or a precursor of such a group $G_1$.

It is clear for one skilled in the art that the group $G_1$ or the precursor of such a group is different from the function involved in the covalent bond with the surface of the nanotube.

In a first alternative of the invention, the molecule bearing a group $G_1$ capable of reacting with said chemical compound or comprising a precursor of such a group (designated hereafter as molecule M) to be grafted on the carbon nanotubes corresponds to any organic molecule capable, under certain conditions, of being grafted to the surface of a carbon nanotube by a radical reaction such as radical chemical grafting, said molecule M further comprising a group $G_1$ capable of reacting with said chemical compound or a precursor of such a group. Such molecules M generally include at least one functional group capable of reacting with a radical.

The term of «radical chemical grafting» notably refers to the use of molecular entities having an unpaired electron for forming bonds of the covalent bond type with the surface of the nanotube, said molecular entities being generated independently of the surface on which they are intended to be grafted. Thus, the radical reaction leads to the formation of covalent bonds between the surface of the nanotube and the derivative of the grafted molecule M.

By «derivative of the molecule M» is meant within the scope of the present invention, a chemical unit resulting from the molecule M, after the latter has reacted by radical chemical grafting with the surface of the nanotube applied within the scope of the present invention. It is clear for one skilled in the art that the group $G_1$ or the precursor of this group borne by the molecule M is different from the function involved in the covalent bond with the surface of the nanotube.

The molecule bearing a group $G_1$ capable of reacting with said chemical compound or a precursor of such a group (molecule M) to be grafted on the carbon nanotube is advantageously a cleavable aryl salt selected from the group formed by aryl diazonium salts, aryl ammonium salts, aryl phosphonium salts and aryl sulfonium salts, said aryl group bearing a group $G_1$ capable of reacting with said chemical compound or a precursor of such a group. In these salts, the aryl group is an aryl group which may be represented by R as defined hereafter.

Among the cleavable aryl salts, mention may in particular be made of compounds of the following formula (I):

wherein:
A represents an monovalent anion and
R represents an aryl group bearing a group $G_1$ capable of reacting with said chemical compound or a precursor of such a group.

As an aryl group of cleavable aryl salts and notably of compounds of formula (I) above, it is advantageously possible to mention aromatic or hetero-aromatic carbon structures, optionally mono- or poly-substituted, consisting of one or more aromatic or hetero-aromatic cycles each including from 3 to 8 atoms, the hetero-atom(s) may be N, O, P or S. The substituent(s) may contain one or more hetero-atoms, such as N, O, F, Cl, P, Si, Br or S as well as notably $C_1$-$C_6$ alkyl groups. It is clear that, within the scope of the present invention, such carbon structures and/or their optional substituents have to bear at least one group $G_1$ capable of reacting with a given chemical compound or a precursor of such a group.

Within cleavable aryl salts and notably within compounds of formula (I) above, R is preferably selected from aryl groups substituted with electron attractor groups such as $NO_2$, COH, ketones, CN, $CO_2H$, $NH_2$ (as $NH_3^+$), esters and halogens. The more preferred groups R of the aryl type are nitrophenyl and phenyl radicals further bearing a group $G_1$ capable of reacting with a given chemical compound or a precursor of such a group.

Within the compounds of formula (I) above, A may notably be selected from inorganic anions such as halides such as $I^-$, $Br^-$ and $Cl^-$, haloborates such as tetraflouroborate, perchlorates and sulfonates and organic anions such as alcoholates, carboxylates.

As compounds of formula (I), it is particularly advantageous to use a compound selected from the group formed by phenyldiazonium tetrafluoroborate, 4-nitrophenyldiazonium tetrafluoroborate, 4-bromophenyldiazonium tetrafluoroborate, 4-aminophenyldiazonium chloride, 4-aminomethylphenyldiazonium chloride, 2-méthyl-4-chlorophényldiazonium chloride, 4-benzoylbenzenediazonium tetrafluoroborate, 4-cyanophenyldiazonium tetrafluoroborate, 4-carboxy-phenyldiazonium tetrafluoroborate, 4-acetamidophenyl-diazonium tetrafluoroborate, diazonium 4-phenylacetic acid tetrafluoroborate, 2-méthyl-4-[(2-methylphenyl)diazenyl]benzenediazonium sulfate, 9,10-dioxo-9,10-dihydro-1-anthracenediazonium chloride, 4-nitronaphthalenediazonium tetrafluoroborate and naphthalenediazonium tetrafluoroborate, all these compounds being, if necessary, substituted with a group capable of reacting with the chemical compound to be detected or a precursor of such a group. Indeed, it is clear that if, among the compounds listed above, certain compounds do not have any group $G_1$ capable of reacting with a given chemical compound or a precursor of such a group, such a group or such a precursor will have to be introduced into said compounds, for example by means of a substitution so that they become usable within the scope of the present invention.

In a second alternative of the invention, the molecule bearing a group $G_1$ capable of reacting with a chemical compound or comprising a precursor of such a group and grafted on the carbon nanotubes is a polymer or copolymer mainly derived from several identical and/or different monomer units, said polymer or copolymer bearing at least one group $G_1$ capable of reacting with said chemical compound or a precursor of such a group.

Advantageously, the totality or part of the monomer units applied within the scope of the present invention are polymerizable monomers via a radical route. By «polymerizable monomers via a radical route» are meant monomers capable of polymerizing under radical conditions after initiation by a radical chemical entity. Typically, these are molecules including at least one bond of the ethylene type, i.e. molecules of the ethylene type. Vinyl monomers, notably the monomers described in international applications WO 2005/033378 and WO 2006/097611 are particularly relevant [20, 21].

According to a particularly advantageous embodiment of the invention, the vinyl monomer(s) is/are selected from monomers of the following formula (II):

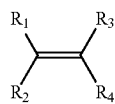

wherein the groups $R_1$ to $R_4$, either identical or different, represent a non-metal monovalent atom such as a halogen atom, a hydrogen atom, a saturated or unsaturated chemical group, such as an alkyl, aryl group, a nitrile, a carbonyl, an amine, an amide or a —$COOR_5$ group wherein $R_5$ represents a hydrogen atom or a $C_1$-$C_{12}$ or preferably $C_1$-$C_6$ alkyl group.

The monomers of the formula (II) above are in particular selected from the group formed by vinyl acetate, acrylonitrile, methacrylonitrile, methyl methacrylate, ethyl methacrylate, butyl methacrylate, propyl methacrylate, hydroxyethyl methacrylate, hydroxypropyl methacrylate, glycidyl methacrylate and their derivatives; acrylamides and notably amino-ethyl, propyl, butyl, pentyl and hexyl methacrylamides, cyanoacrylates, di-acrylates and di-methylacrylates, tri-acrylates and tetra-methacrylates (such as pentaerythritol tetra-methacrylate), styrene and its derivatives, para-chlorostyrene, pentafluoro-styrene, N-vinyl-pyrrolidone, 4-vinyl pyridine, 2-vinyl pyridine, vinyl, acryloyl or methacryloyl halides, divinylbenzene (DVB), and more generally vinyl cross-linking agents or based on acrylate, methacrylate, and their derivatives.

The polymer or copolymer may be grafted on the surface of the nanotube either directly or indirectly. By «direct grafting», is meant the case when the covalent bond between the surface of the nanotube and the polymer or copolymer involves an atom of one of the monomers making up said polymer or copolymer and an atom of the surface of said nanotube. By «indirect grafting», is meant the case when a molecular entity separates the polymer from the surface of the nanotube. Thus, this molecular entity is bound through a covalent bond to the surface of the nanotube and through another covalent bond to the polymer or copolymer. Such a molecular entity is advantageously derived from a molecule M as defined earlier except that the molecular entity does not necessarily comprise a group $G_1$ or a precursor of such a group. More particularly, this molecular entity corresponds to a derivative of the derivative of the molecule M as defined earlier except that the molecular entity does not necessarily comprise a group $G_1$ or a precursor of such a group. Indeed, once said derivative has reacted by radical chemical grafting with the surface of the nanotube, the grafted derivative reacts by a radical reaction with a monomer as defined earlier. In this alternative, it is clear that the polymer may optionally contain, between some of the monomer units making it up, one or more molecular entities used for grafting said polymer to the surface of the nanotube.

The thereby obtained polymer or copolymer grafted to the surface of the nanotube bears at least one group $G_1$ capable of reacting with said chemical compound or a precursor of such a group. This group may notably be borne by at least one of the monomer units. Thus, as an example, for a polymer or copolymer comprising monomers of formula (II), at least one of these monomers comprises at least one of the groups $R_1$ to $R_4$ which bears said group capable of reacting with the chemical compound to be detected and which is not involved in radical polymerization. Alternatively, the obtained polymer or copolymer may, if necessary, be substituted with a group $G_1$ or a precursor of such a group.

The thereby obtained polymer or copolymer film grafted at the surface of the nanotube has a length of less than 50 nm, advantageously less than 40 nm, notably less than 30 nm and in particular, less than 20 nm.

The group $G_1$ capable of reacting with a chemical compound to be detected, applied within the scope of the present invention, may be any type of group, which, when it is put into the presence of the chemical compound to be detected, is capable of reacting with the latter, either directly or not.

In a first embodiment of the present invention, the group $G_1$ has affinity for the chemical compound and reacts with the latter. During this reaction, bonds, notably weak bonds of the Van der Waals type appear between the group $G_1$ and the chemical compounds. In this case, the group $G_1$ is capable of reacting with the chemical compound so as to form a complex with the latter or to physically absorb the chemical compound on the group $G_1$.

In a second embodiment of the present invention, the group $G_1$ reacts with the chemical compound, either directly or not, in order to give another group $G_2$ different from the group $G_1$. During the reaction in the presence of the chemical compound, the group $G_1$ may be substituted with a different group which corresponds to the $G_2$ group. Alternatively, in the presence of the chemical compound, at least one atom may be added to or removed from the group $G_1$ in order to transform it into a different group which corresponds to the group $G_2$, the latter may either be electrically charged or not.

The physical absorption of the chemical compound on the group $G_1$, the forming of a complex with the group $G_1$ and the chemical compound or the replacement of the group $G_1$ with a group $G_2$ have the consequence of modifying the resistance of the nanotube, as compared with the resistance of the nanotube comprising the group $G_1$ in the absence of the chemical compound.

Such groups $G_1$ capable of being applied within the scope of the present invention generally correspond to groups including at least one covalent bond between a hetero-atom and another element corresponding to a carbon, a hydrogen or another hetero-atom. The hetero-atom(s) is(are) generally selected from N, O, S, Cl, Br and Si.

Advantageously, said group $G_1$ is selected from the group formed by the hydroxyl, thiol, azide, epoxide, azyridine, amine, nitrile, isocyanate, thiocyanate, nitro, amide, halide notably alkyl halide, carboxylic acid and ester functions.

By «precursor of a group $G_1$ capable of reacting with a chemical compound», is meant within the scope of the present invention, a group which by its nature, cannot directly react with the chemical compound but which may, through a simple chemical reaction, give the group $G_1$. Such a precursor may for example be a $G_1$ group protected by a protective group. One skilled in the art is aware of different types of precursors and different methods for transforming them into particular $G_1$ groups capable of reacting with a given chemical compound.

As examples, Table 1 shows the chemical compounds, the groups $G_1$ which are associated with them, the reaction applied and optionally the optional groups $G_2$ obtained in the presence of said compound, R' representing a portion of the molecule bearing the group $G_1$.

TABLE 1

| Chemical compound to be detected | Formula of said compound | Grafted chemical function | Reaction |
|---|---|---|---|
| Chlorine | $Cl_2$ | $R'-NH_2$ | $Cl_2 + R'-NH_2 \rightarrow R-NHCl + HCl$ |
| Thionyl chloride | $SOCl_2$ | $R'-OH$ $R'-NH_2$ | $R'-OH + SOCl_2 \rightarrow R'-Cl + SO_2 + HCl$ |
| Ammonia | $NH_3$ | —COOH PHEMA(poly(2-hydroxyethyl) methacrylate) PAA poly(acrylic acid) | Acid-base |
| Sarin | $C_4H_{10}O_2PF$ | $R'-F$ (fluorinated polymers) | Affinity between fluorinated compounds |
| Hydrocyanic acid | HCN | P4PV poly(4-vinylpyridine) $R'-NH_2$ | Acid-base |
| Phosphine | $PH_3$ | (1) —COOH (2) —$R'-CH_2$—X (X: Cl, Br, I) | (1) Acid-base (2) $PH_3 + R'-CH_2-X \rightarrow H_3P^- \, ^+CH-R'$ |

The device according to the present invention further comprises
a support,
and two electrodes positioned on said support,
the carbon nanotubes which the device of the present invention comprises, ensuring electric contact between both of these electrodes.

Indeed, the device of the invention is a resistive sensor, i.e., which uses the resistance of the carbon nanotubes with several graphene layers as a transduction means for detecting a given chemical compound. The resistance of the grafted carbon nanotubes which ensure the contact between both of these electrodes, is measured. Under the effect of a chemical compound reacting with the group $G_1$ borne by the grafted molecules on the carbon nanotubes, in order to be physically absorbed to said group $G_1$, to form a complex with said group $G_1$ or to give the group $G_2$, the resistance of the nanotubes varies in a specific way which depends on the nature and on the content of the detected compound.

The support which the device according to the present invention comprises may be any support allowing application of the present invention. It may also be substantially planar and with any shape such as a square, rectangular, round or oval shape. Advantageously, it may be in an insulating material such as silica, glass, polymer, plastic, etc. . . . .

The electrodes which the device according to the present invention comprises, consist of a conducting material. Said electrodes are in any metal or metal material, advantageously selected from the group formed by Au, Pd, Pt, Al, Cr, Ni, Ti, ITO, W and steel, in a multi-layer material or in a metal/metal material composite material such as Ti/Au, Cr/Au, Ti/Pd or Ti/Au.

The electrodes may also be of any shape allowing application of the present invention. Advantageously the electrodes applied in the device of the invention have an either spiral or concentric interdigitated comb configuration. Preferably, the electrodes which the device according to the invention comprises, have an interdigitated comb configuration advantageously comprising for each electrode, at least 3 arms, notably at least 5 arms and, in particular at least 10 arms.

Any technique known to one skilled in the art allowing two electrodes to be prepared at the surface of a support may be used within the scope of the present invention. However, the use of long carbon nanotubes with several graphene layers advantageously having a length greater than or equal to 20 µm, gives the possibility of contemplating large interelectrode spacings. Advantageously, these spacings are comprised between 1 and 300 µm; notably comprised between 5 and 200 µm; in particular, greater than 20 µm and, more particularly, greater than 50 µm. With this, it is possible to have access to simple and relatively inexpensive simple techniques for elaborating electrodes, such as metal deposition techniques in vacuo for example by thermo-evaporation by plasma (or PECVD «Plasma-Enhanced Chemical Vapor Deposition») or by sputtering.

As an exemplary method for preparing the electrodes of the device according to the present invention, the latter are deposited beforehand on a glass plate in an evaporation chamber. They consist of a stack of two thin layers: a thin metal layer resting on a chromium or titanium adherence layer of a few nanometers which ensures adhesion with the surface of the glass.

The carbon nanotubes which the device of the present invention comprises, have an orientation which is substantially perpendicular with respect to the two electrodes. Further, these nanotubes are arranged homogeneously on said electrodes. By «homogeneous arrangement» is meant that the carbon nanotubes are regularly distributed between the electrodes with few or no clusters of nanotubes. FIG. 8B is an illustration of a homogeneous arrangement of nanotubes. Thus, the use of a technique such as the dielectrophoresis technique for positioning the nanotubes on the electrodes leads to a homogeneous arrangement of the carbon nanotubes, preferentially oriented perpendicularly between the advantageously interdigitated electrodes. With this technique, it is also possible to only use a small amount of carbon nanotubes for ensuring the contact between the electrodes, which reduces the manufacturing costs of the device and increases the specific surface area in contact with ambient air.

Finally, the device, object of the present invention, further comprises means with which an electric current or a given potential may be applied to the electrodes and the resistance of the device may be controlled. These means advantageously comprise one or more components selected from
an electric source such as a battery,
means for connecting the electrodes to said electric source such as a circuit,
control means and measurement means in order to be able to adjust, track and/or monitor the potential applied to the electrodes and/or the resistance of the nanotubes.

FIG. 1 is a schematic illustration of a device according to the present invention. This device consists of a glass plate corresponding to the support (1), of two interdigitated conducting electrodes (2), each having three arms, of grafted multi-sheet carbon nanotubes (3) achieving electric contact between both electrodes and means (4) with which the changes in the resistance of the nanotubes and therefore in the resistance of the device may be tracked. The useful spacing between the electrodes is comprised between 1 and 300 µm. The electrode comb occupies a surface area of about 100 $mm^2$ on a support, the surface of which is comprised between 400 $mm^2$ and 10 $cm^2$, notably between 400 $mm^2$ and 1 $cm^2$.

The device, object of the present invention allows selective and low content detection (<1 ppm) of notably toxic, gaseous chemical agents, such as in particular chlorine. This detection is possible at a moderate temperature, advantageously below 100° C., notably below 80° C., in particular below 60° C., and more particularly, below 40° C. More preferably, the detection is carried out at room temperature, i.e. at a temperature comprised between 20° C.±5° C. Under such conditions, the chlorine, as an example, may be detected for contents below 27 ppb. By being able to carry out detection at room temperature, it is possible to avoid the addition of a heating system to the device for its proper operation.

An additional criterion will be added to the features discussed earlier of the device according to the present invention. The initial resistance of the device, which is a major parameter for its proper operation and for the reproducibility of the detections and quantifications, may be finely controlled (±100Ω) via the concentration of the dispersion from which the carbon nanotubes are taken in order to be deposited on the electrodes. Advantageously, it is possible to manufacture devices according to the present invention in series having the same features. Individualized calibration i.e. for each manufactured device, may therefore be avoided.

The present invention also relates to a system comprising at least two devices as defined earlier. Advantageously, such a system comprises at least three devices, notably at least 5 devices, in particular at least 10 devices and, more particularly, at least 15 devices such as those defined earlier. Among these devices, some or even all of them are differentiated by the targeted gas, i.e. by the group $G_1$ borne by the nanotubes. The devices which the system according to the invention has, may be assembled and they operate in parallel. The system then becomes a multi-sensor system, commonly called an «electronic nose». In fine, this system allows the detection of many chemical agents, each chemical agent having a response specific to each device making up the system.

The present invention also relates to the use of a device or of a system as defined earlier for detecting and optionally quantifying one or more gaseous chemical compound(s). Any gaseous chemical compound may be detected and/or quantified by using a device or a system according to the invention. Advantageously, said gas chemical compound is selected from the group formed by volatile organic compounds, hydrogen, carbon monoxide, carbon dioxide, chlorine and chlorinated compounds, ammonia, organo-phosphorus gases such as sarin and di-methylmethylphosphonate, hydrocyanic acid, thionyl chloride, phosphine, tetrahydrofurane, methane and dimethylmethyl phosphonate.

The present invention therefore relates to a method for detecting and optionally quantifying a gaseous chemical compound consisting of putting a device according to the invention in the environment in which said compound is present or likely to be present, and of tracking the change of at least one electric characteristic of the device. As examples, this characteristic may be the resistance, the impedance and/or the capacitance of the device.

Finally, the present invention relates to a method for preparing a device intended to detect at least one chemical compound as defined earlier.

Said method comprises a step consisting of depositing on two electrodes, at least one carbon nanotube with several layers of graphene, on which is grafted at least one molecule bearing a group $G_1$ capable of reacting with said chemical compound or a precursor of such a group $G_1$, so that said carbon nanotube ensures electric contact between said electrodes.

Any known technique for depositing a carbon nanotube prepared and grafted beforehand may be used within the scope of the present invention. However, considering the already mentioned advantages, said deposition is carried out by dielectrophoresis. Advantageously, said deposition step consists of (i) positioning on the electrodes a given volume of a solution $S_1$ in which carbon nanotubes prepared and grafted beforehand as defined earlier are dispersed; (ii) of applying a peak-to-peak sinusoidal alternating voltage between the electrodes and (iii) of drying the device obtained in step (ii) in an oven.

During step (i), the applied electrodes are such as defined earlier and are positioned on a support as defined earlier. Therefore, the term of «device» comprises the support, the electrodes and the grafted carbon nanotubes positioned on the electrodes. The solution $S_1$ in which the grafted carbon nanotubes are dispersed, contains, as a solvent, an organic solvent or alternatively an aqueous solvent containing a surfactant. Any organic solvent known to one skilled in the art may be used. However, this solvent is advantageously selected from the group formed by methanol, ethanol, propanol, isopropanol, toluene, ethyl acetate, tetrahydrofurane, acetone, dimethylformamide and isopropyl 1,4-dioxane. In the case of a solution $S_1$ containing as a solvent an aqueous solvent containing a surfactant, any surfactant known to one skilled in the art may be used. Advantageously, said surfactant, belongs to a type selected from anionic surfactants, cationic surfactants, zwitterionic surfactants and neutral (non-ionic) surfactants and, notably the surfactants described in international application WO 2008/078052 [22].

The grafted carbon nanotubes are present, in the solution $S_1$, in an amount comprising between 0.1 and 1,000 mg/L, notably between 1 and 500 mg/L, in particular between 5 and 250 mg/L, and more particularly between 10 and 100 mg/L of solution $S_1$.

The grafted carbon nanotubes may be maintained and dispersed in the solution $S_1$ by any technique known to one skilled in the art. As examples, mention may be made of simple stirring with ultrasound, manual stirring, mechanical stirring by means of mechanical stirrers with rods, blades, propellers, etc., . . . or a combination of the stirring techniques. It should be noted that the fact that the carbon nanotubes are grafted, promotes their dispersion in the solution $S_1$ (see Example 1 hereafter).

The volume of solution $S_1$ deposited on the electrodes is advantageously comprised between 0.1 μL and 10 mL, notably between 0.5 μL and 1 mL, in particular, between 1 μL and 100 μL and, most particularly between 5 μL and 50 μL. The solution $S_1$ is advantageously deposited in the form of one or several drops.

Step (ii) is advantageously applied during the evaporation of the meniscus, formed by the drop(s) of solution $S_1$ deposited on the electrodes. The peak-to-peak sinusoidal alternating voltage applied between the electrodes is comprised between 5 and 50 V, notably between 10 and 30 V and in particular is of the order of 20 V, (i.e. 20±5 V). The frequency range used during step (ii) is comprised between 100 kHz and 100 MHz and notably between 5 to 30 MHz.

During the step (iii), the device is put into an oven at a temperature comprised between 50 and 200° C., notably between 100 and 150° C., and in particular, of the order of 120° C. (i.e. 120±5° C.), for a duration comprised between 15 min and 36 hrs, notably between 8 and 24 hrs and, in particular, of the order of 12 hrs (i.e. 12 h±30 min) before use. The initial resistance range for which the operation of the chemical sensor is optimum (best sensitivity, signal-to-noise ratio and stability) is located between 100 and 500Ω.

The method of the present invention comprises a preliminary step consisting of grafting on the carbon nanotubes, said molecule bearing a group $G_1$ capable of reacting with a given chemical compound or a precursor of such a group.

Any grafting technique known to one skilled in the art may be used within the scope of the present invention. However, an advantageously applied technique is the one described in international application WO 2008/078052 [22].

Thus, this preliminary grafting step consists of submitting, in the presence of at least one carbon nanotube, a solution $S_2$ containing at least one molecule bearing a group $G_1$ capable of reacting with a given chemical compound or a precursor of this group or a precursor of such a molecule, to conditions allowing the formation of at least one radical entity from said molecule or said precursor.

The solution $S_2$ applied in the grafting step of the method according to the present invention contains as a solvent, a solvent which may be:
- either a protic solvent, i.e. a solvent which includes at least one hydrogen atom capable of being released as a proton and advantageously selected from the group formed by water, deionized water, either acidified or basic distilled water, acetic acid, hydroxyl solvents such as methanol and ethanol, liquid glycols of low molecular weight such as ethylene glycol, and mixtures thereof;
- or an aprotic solvent, i.e. a solvent which is not capable of releasing a proton and of accepting one under non-extreme conditions and advantageously selected from dimethylformide (DMF), acetone, acetonitrile and dimethylsufoxide (DMSO);
- or a mixture of at least one protic solvent and of at least one aprotic solvent.

The conditions allowing the formation of at least one radical entity in the grafting step of the method of the present invention are conditions which allow the formation of radical entities in the absence of the application of any electric voltage to the reaction mixture comprising a solvent, at least one nanotube, at least one molecule bearing a group $G_1$ capable of reacting with a given chemical compound or a precursor of this group or a precursor of such a molecule.

These conditions involve parameters such as for example, the temperature, the nature of the solvent, the presence of a particular additive, stirring, pressure while the electric current is not involved during the formation of the radical entities. The conditions allowing the formation of radical entities are numerous and this type of reaction is known and studied in detail in the prior art.

For example, it is thereby possible to act on the thermal, kinetic, chemical, photochemical or radiochemical environment of the molecule bearing a group $G_1$ capable of reacting with a given chemical compound or a precursor of this group (or a precursor of such a molecule), in order to destabilize it so that it forms a radical entity. Of course it is possible to simultaneously act on several of these parameters.

Within the scope of the present invention, the conditions allowing the formation of radical entities during the grafting step according to the invention are typically selected from the group formed by thermal conditions, kinetic conditions, chemical conditions, photochemical conditions, radiochemical conditions and their combinations to which the molecule or its precursor are subject. Advantageously, the conditions applied within the scope of the grafting step of the method according to the present invention are selected from the group formed by thermal conditions, chemical conditions, photochemical conditions, radiochemical conditions and their combinations with each other and/or with kinetic conditions. The conditions applied within the scope of the grafting step of the method according to the method of the invention are more particularly chemical conditions.

The thermal environment depends on temperature. It is easy to control it with heating means customarily used by one skilled in the art. The use of a thermostated environment has a particular advantage since it allows accurate control of the reaction conditions.

The kinetic environment essentially corresponds to the stirring of the system and to the frictional forces. The question here is not the agitation of the molecules per se (elongation of bonds etc.,) but the overall motion of the molecules.

Thus, during said grafting step, the solution $S_2$ is subject to mechanical stirring and/or to a treatment with ultrasound. In a first alternative, the suspension applied during the grafting step is subject to a high speed of rotation by means of a magnetic stirrer and of a magnetized bar and this, for a duration comprised between 5 mins and 24 hrs of stirring, notably comprised between 10 min and 12 hrs and in particular between 15 min and 6 hrs. In a second alternative, the suspension applied during the grafting step is subject to a treatment with ultrasound by using an ultrasound pan, typically with an absorption of 500 W and at a frequency of 25 or 45 kHz and this, for a duration comprising 5 mins and 24 hrs of stirring, notably comprised between 15 mins and 12 hrs, and, in particular between 30 mins and 6 hrs.

Finally the action of various radiations such as electromagnetic radiations, γ radiations, UV rays, electron or ion beams may also sufficiently destabilize the molecule M so that it forms radicals. The wavelength used will be selected, without any inventive effort, according to the molecule M used. For example, a wavelength of about 306 nm will be used for 4-hexylbenzediazonium.

Within the scope of chemical conditions, one or more chemical initiators are used in the reaction medium. The presence of chemical initiators is often coupled with non-chemical environmental conditions, as discussed above. Typically, a chemical initiator, the stability of which is smaller than that of the molecule or the precursor applied under selected environmental conditions, will develop into an unstable form which will act on the latter and will generate from them the formation of radical entities. It is also possible to use chemical initiators, the action of which is not essentially related to the environmental conditions and which may act over vast ranges of thermal or even kinetic conditions. The initiator will preferably be adapted to the environment of the reaction, for example, to the solvent used.

There exist many chemical initiators. Three types are generally distinguished depending on the environmental conditions used:
- thermal initiators, the most common of which are peroxides or azo compounds. Under the action of heat, these compounds dissociate into free radicals. In this case, the reaction is carried out at a minimum temperature corresponding to the one required for forming radicals from the initiator. This type of chemical initiators is generally used specifically in a certain temperature interval, depending on their decomposition kinetics;
- photochemical or radiochemical initiators which are excited by radiation triggered by irradiation (most often by UV, but also by γ radiations or by electron beams) allow production of radicals by more or less complex mechanisms. $Bu_3SnH$ and $I_2$ belong to the photochemical or radiochemical initiators;

essentially chemical initiators, this type of initiators acting rapidly and under normal conditions of temperature and of pressure on the molecule or its precursor in order to allow it to form radicals. Such initiators generally have a redox potential which is below the potential for reducing said molecule or said precursor used under reaction conditions. Depending on the nature of the molecule or its precursor, this may thus be a reducing metal for example, such as iron, zinc, nickel; a metallocene; an organic reducing agent such as hypophosphorous acid ($H_3PO_2$) or ascorbic acid; an organic or inorganic base in sufficient proportions for allowing destabilization of the molecule or of its precursor. Advantageously, the reducing metal used as a chemical initiator appears in a finely divided form, such as metal wool (also more commonly called «scales») or metal filings. Generally, when an organic or inorganic base is used as a chemical initiator, a pH greater than or equal to 4 is generally sufficient. Structures of the radical reservoir type such as polymeric matrices irradiated beforehand with an electron beam or with a heavy ion beam and/or with the whole of the irradiation means mentioned earlier, may also be used as chemical initiators for destabilizing the molecule or its precursor and leading to the formation of radical entities from the latter.

During the grafting step of the method according to the present invention, the carbon nanotubes are present in the solution $S_2$, in an amount comprised between $1.10^{-5}$ g/mL and $1.10^{-1}$ g/mL of solution $S_2$ and advantageously between $1.10^{-4}$ g/mL and $1.10^{-2}$ g/mL of solution $S_2$.

Further, during the grafting step of the method according to the present invention, the concentrations of the solid compounds used, notably, the carbon nanotubes and the chemical initiators such as iron wool, are present in the solution $S_2$, in an amount comprised between $1.10^{-5}$ g/mL and 1 g/mL of solution $S_2$ and advantageously between $1.10^{-4}$ g/mL and $1.10^{-1}$ g/mL of solution $S_2$.

More particularly, the method according to the invention comprises the following successive steps:

a) optionally annealing carbon nanotubes with several graphene layers, notably under the conditions described earlier, b) putting said nanotubes optionally annealed in step (a) in contact with a solution $S_2$ containing at least one molecule bearing a group $G_1$ capable of reacting with said chemical compound or a precursor of such a group or at least one precursor of the latter molecule;

c) submitting the mixture of step (b) to non-electrochemical conditions so as to graft on said nanotubes, said molecule or said precursor;

d) recovering the grafted nanotubes obtained after step (c) and depositing them on two electrodes, notably by dielectrophoresis.

The molecule bearing a group $G_1$ capable of reacting with a given chemical compound or a precursor of such a group applied in the method according to the invention, is advantageously a molecule M as defined earlier.

By «precursor of the latter», is meant within the scope of the present invention a precursor of a molecule bearing a group $G_1$ capable of reacting with a given chemical compound or a precursor of this group.

In a first alternative, by «precursor of the latter» is more particularly meant a molecule separated from the molecule M by a single operation step easy to apply.

Generally, the precursors have greater stability than the molecule M under the same environmental conditions. One skilled in the art is aware of various «precursor of a molecule M»/«molecule M» pairs. Thus, for example aryl amines are precursors of aryl diazonium salts. Indeed, by simple reaction, for example with $NaNO_2$ in an acid aqueous medium, or with $NOBF_4$ in an organic medium, it is possible to form the corresponding aryl diazonium salts.

As a precursor of molecule M, mention may notably be made of precursors of aryl diazonium salts, said precursor of said molecule is of the following formula (II):

R being an aryl group as defined earlier.

As a precursor of molecule M which may be applied within the scope of the present invention, it is particularly advantageous to use a precursor selected from the group formed by phenylamine, 4-nitrophenylamine, 4-bromophenylamine, 4-aminophenyl-amine, 2-methyl-4-chlorophenylamine, 4-benzoylbenzene-amine, 4-cyanophenylamine, 4-carboxyphenylamine, 4-acetamidophenylamine, diazonium 4-phenylacetic acid tetrafluoroborate, 2-methyl-4-[(2-methyl-phenyl)-diazenyl]amine, 9,10-dioxo-9,10-dihydro-1-anthracene-amine, 4-nitronaphthalene-amine and naphthalene-amine, all these compounds being, if necessary, substituted with a group $G_1$ capable of reacting with a given chemical compound or a precursor of such a group. Indeed, it is clear that if, among the compounds listed above, certain compounds do not have any group $G_1$ capable of reacting with a given chemical compound or a precursor of such a group, such a group will have to be introduced into said compounds by means of a substitution so that they become usable within the scope of the present invention.

One skilled in the art will know how to determine, without any inventive effort, the adequate conditions to be used, during the grafting step of the method (i.e. step (c)), depending on the type of precursor applied and on the molecule M to be obtained. Thus, the transformation of amine functions into diazonium functions may be carried out in a single step by means of $NaNO_2$ in an acid aqueous medium, or by means of $NOBF_4$ in an organic medium.

In a second alternative, notably applied to the case when the molecule bearing a group $G_1$ capable of reacting with a given chemical compound is a polymer or a copolymer, the precursor of the latter is:

either a monomer which is polymerizable via a radical route and notably monomers of formula (II) as defined earlier, or an adhesion primer which initiates the radical reaction with which it is possible to end up with the polymer or the copolymer, such an adhesion primer may be a molecule M as defined earlier, except that the molecule M should not necessarily bear a group $G_1$ capable of reacting with a given chemical compound or a precursor of such a group, or a precursor of such an adhesion primer and, more particularly a precursor of a molecule M as defined earlier, except that said precursor should not necessarily bear a group $G_1$ capable of reacting with a given chemical compound or a precursor of such a group, or one of their mixtures.

The amount of molecules M, of precursors of molecules M, of adhesion primers or precursors of adhesion primers in the solution $S_2$ may vary depending on what is desired by the experimenter. This amount is advantageously comprised, within the solution $S_2$, between about $10^{-6}$ and 5 M, preferably between $5.10^{-2}$ and $10^{-1}$ M.

The amount of polymerizable monomers in the solution $S_2$ may vary depending on what is desired by the experimenter. This amount may be greater than the solubility of the relevant monomer in the solvent of the solution $S_2$ used and may represent for example 18 to 40 times the solubility of said monomer in the solution $S_2$ at a given temperature, generally room temperature or that of the reaction. Under these conditions, it is advantageous to use means allowing dispersion of the monomer molecules in the solution, such as a surfactant or ultrasound. The usable surfactants are notably anion surfactants, cationic surfactants, zwitterionic surfactants, amphoteric surfactants and neutral (non-ionic) surfactants and, notably the surfactants described in the international application WO 2008/078052 [22].

During the step (b) of the method according to the present invention, the carbon nanotubes are put into contact with at least one molecule M as defined earlier or at least one precursor of the latter as defined earlier. This putting into contact is a standard step in chemistry.

Step (c) of the method according to the present invention corresponds to the grafting step as defined earlier.

As the molecule to be grafted or its precursors are present in a large amount in the solution $S_2$, the grafting step may be stopped before all the molecules are attached onto the carbon nanotubes. One skilled in the art is aware of various techniques with which the grafting step may be stopped and will know how to determine the most suitable technique depending on the molecule to be grafted or on its precursors applied in step (c). As examples of such techniques, mention may be made of a change in pH of the solution $S_2$ notably by adding a basic solution thereto (for example basic water with a pH above 10), a removal of the molecules to be grafted or of its precursors present in the solution $S_2$ (for example, by filtration, by precipitation or by complexation).

In the preparation method according to the present invention, step (d) first of all consists of recovering the grafted carbon nanotubes following step (c) before placing them in the solution $S_1$ and depositing them on the electrodes as described earlier. Any technique allowing recovery of the carbon nanotubes may be applied within the scope of the present invention.

As examples, mention may be made of the recovery of nanotubes by filtration of the solution applied in step (c) notably by using Teflon membranes or paper filters in folded crepe. It may be necessary to repeat this filtration step several times.

Further, before suspending the thereby recovered grafted carbon nanotubes, drying of these nanotubes may be considered. This drying step may be applied in an oven or stove and this at a temperature comprised between 80° C. and 150° C. and notably comprised between 100° C. and 130° C.

Other features and advantages of the present invention will further become apparent to one skilled in the art upon reading through the examples given below as an illustration and not as a limitation, with reference to the appended figures.

SHORT DESCRIPTION OF THE DRAWINGS

FIG. 3 shows optical microscopy images of multi-walled carbon nanotubes deposited on interdigitated electrodes by dielectrophoresis after deposition of a suspension drop (FIG. 3A) and without dielectrophoresis after depositing sixteen suspension drops (FIG. 3B).

FIG. 4 shows optical microscopy images of multi-walled carbon nanotubes deposited on the interdigitated electrodes by dielectrophoresis after depositing a suspension drop (5 mg/L), the carbon nanotubes being either crude (FIG. 4A), or annealed (FIG. 4B).

FIG. 5 shows the curves for detecting chlorine at a content of a 100 ppb (diluted in nitrogen) of sensors based on «crude» and «annealed» nanotubes. The normalized resistance, i.e. the measured resistance divided by the initial resistance, is plotted in ordinates versus the time expressed in minutes.

DETAILED DESCRIPTION OF CERTAIN ILLUSTRATIVE EMBODIMENTS

Example 1: Preparation of Suspensions of Long Multi-Sheet Carbon Nanotubes

The suspensions of different concentrations (1~100 mg/L) of long multi-sheet carbon nanotubes (400 µm) in isopropanol are prepared with an ultrasonic probe. In this example, the suspensions are subject to ultrasounds for 8 minutes with a power of 250 W. Up to 10 mg/L, the suspensions are (visibly) stable for several hours.

For more concentrated suspensions, flocculation or sedimentation of the nanotubes appears after a few tens of minutes. The suspensions having a nanotube concentration of 5 to 10 mg/L are used for making sensors based on the use of non-functionalized nanotubes.

The suspensions of functionalized nanotubes, as for them, are stable in isopropanol for a few hours or even a few days at concentrations of less than 100 mg/L. The suspensions having a nanotube concentration in the range from 20 to 100 mg/L are used for preparing sensors based on functionalized nanotubes.

Example 2: Effect of Dielectrophoresis During the Preparation of Sensors According to the Invention The applied dielectrophoresis conditions are a 5 MHz sinusoidal 20 V peak-to-peak voltage.

Figure 1:
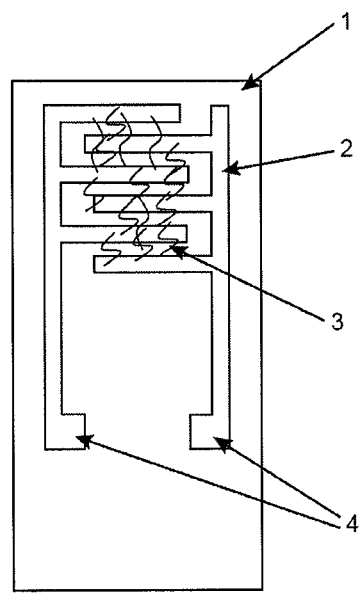
FIG. 1 is a schematic illustration of the principle of a device according to the present invention.
Figure 2:
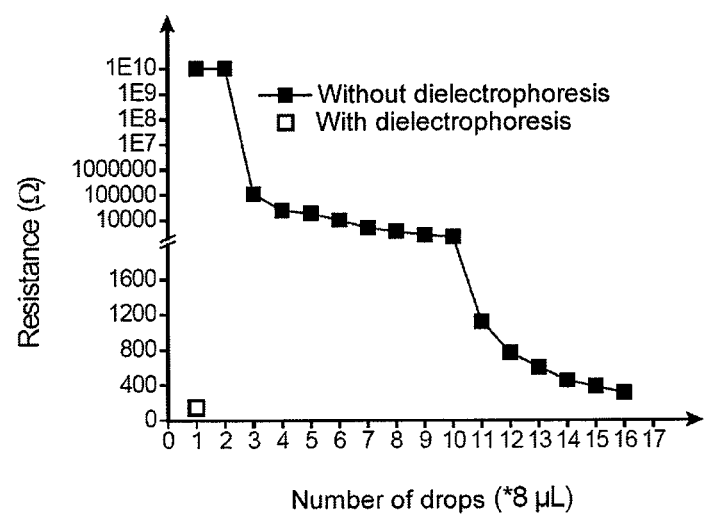
FIG. 2 shows the initial resistance of the sensor versus the number of drops (8 µL per drop) deposited on the electrodes with and without dielectrophoresis.

The initial resistance of a sensor depending on the number of drops (8 µL per drop) deposited on the electrodes with and without dielectrophoresis was investigated (FIG. 2). The nanotube concentration for the suspension used for both sensors is 5 mg/L.

In this example, with dielectrophoresis, it is possible to reduce by a factor of 16 the number of deposited drops in order to attain the proper initial resistance value.

Further, the optical microscopy image of multi-walled carbon nanotubes deposited on the interdigitated electrodes by dielectrophoresis, after depositing a suspension drop, reveals that the nanotubes are quasi individual and have a preferential orientation perpendicular to the electrodes (FIG. 3A). The nanotubes are, on the contrary, organized as a cluster as viewed on the optical microscopy image of the multi-walled carbon nanotubes deposited on the interdigitated electrodes without any dielectrophoresis, after depositing sixteen drops of the suspension (FIG. 3B).

Example 3: Effect of Annealing on Carbon Nanotubes

This example aims at comparing a device based on «crude» carbon nanotubes and a device based on carbon nanotubes annealed at 2,000° C. for one hour under argon.

FIGS. 4A and 4B are optical microscopy images obtained for respectively «crude» or «annealed» multi-walled carbon nanotubes, deposited on the interdigitated electrodes by dielectrophoresis after depositing one drop of suspension (5 mg/L).

The sensitivity of such sensors based on «crude» and «annealed» nanotubes towards chlorine diluted in nitrogen at a content of 100 ppb was also compared. The results shown in FIG. 5 show that the sensitivity ($S=(R-R_0)/R_0$) *100) at 50 mins of the sensor based on «annealed» nanotubes is twice greater, as compared with that of the sensor based on «crude» nanotubes (26 versus 12.5).

Figure 6:
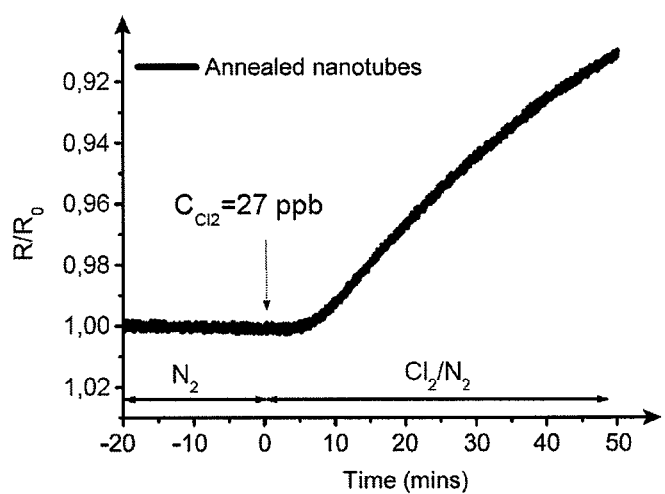
FIG. 6 shows the curve for detecting chlorine at a content of 27 ppb (diluted in nitrogen) by means of a sensor according to the invention based on annealed nanotubes. The normalized resistance, i.e. the measured resistance divided by the initial resistance, is plotted in ordinates versus the time expressed in minutes.

Further, the sensitivity ($S=(R-R_0)/R_0$)*100) towards chlorine diluted in nitrogen at a content of 27 ppb of a sensor based on «annealed» nanotubes and measured at 50 minutes is 7% (FIG. 6).

Example 4: Elaboration of Sensors Based on Multi-Sheet Carbon Nanotubes Functionalized by -Ph-$CH_2$—$NH_2$ Groups The functionalization of the nanotubes is carried out by following the procedure described hereafter.

Fifteen mg of nanotubes are subject to an ultrasound treatment for 8 mins at 250 W in 30 mL of 0.5 M HCl with $3.10^{-3}$ mol of 4-aminobenzyl amine. To this mixture, is then added $3.10^{-3}$ mol of sodium nitrite dissolved in 30 mL of distilled water. Four g of iron powder are added to the whole which is transferred into an ultrasound pan.

After 90 minutes of reaction, the iron powder is removed by means of a magnetic bar and the mixture is filtered and then thoroughly washed with ethanol, acetone and distilled water. The nanotubes are then dried in the oven at 120° C.

The functionalized nanotubes are subject to a treatment with ultrasound again with isopropanol for 8 mins at 250 W in an amount from 20 to 100 mg/L. The suspensions are stable for several hours or even one day.

Figure 7:
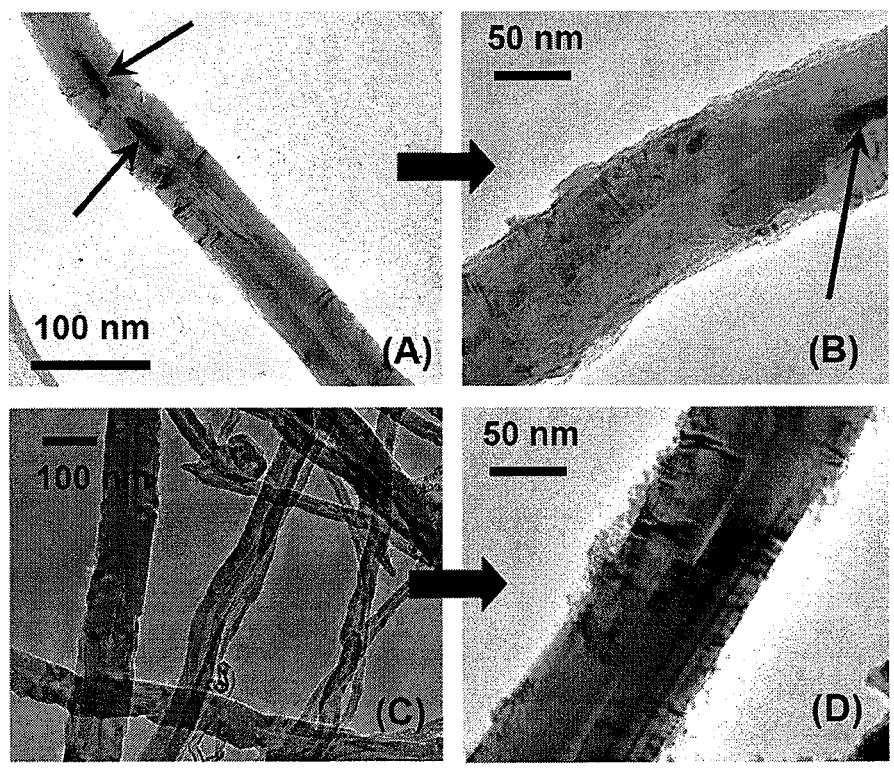
FIG. 7 shows scanning electron microscopy images of «crude» nanotubes (FIG. 7A where the arrows indicate the presence of iron-based particles in the core of the nanotubes), of functionalized «crude» nanotubes (FIG. 7B), of annealed nanotubes (removal of iron) (FIG. 7C) and of functionalized annealed nanotubes (FIG. 7D).

The crude or «annealed» nanotubes, either functionalized or not, are observed by transmission electron microscopy. Iron-based particles are present in the core of non-functionalized «crude» nanotubes (FIG. 7A) and a thin polymer layer (<10 nm) covers the surface of the functionalized «crude» nanotubes (FIG. 7B). The iron was removed from the «annealed» nanotubes (FIG. 7C) and a thin polymer layer (<20 nm) covers the surface of the functionalized «annealed» nanotubes.

Figure 8:
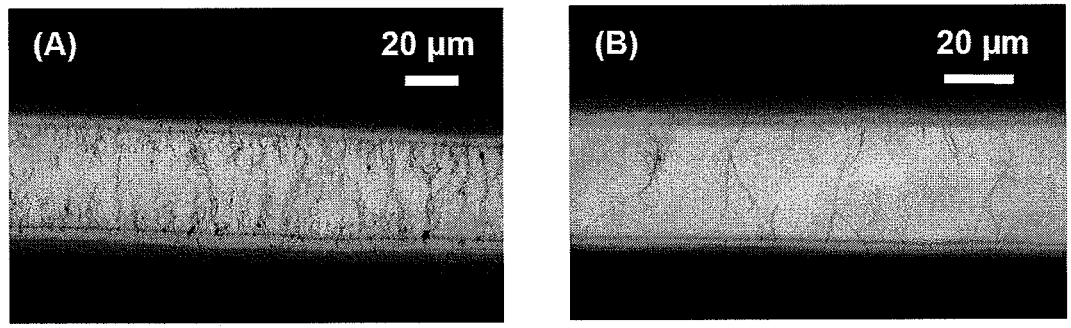
FIG. 8 shows optical microscopy images of crude multi-sheet carbon nanotubes functionalized by groups -Ph-$CH_2$—$NH_2$ (FIG. 8A) or of multi-sheet carbon nanotubes annealed and functionalized with groups -Ph-$CH_2$—$NH_2$ (FIG. 8B).

The crude or «annealed» functionalized (-Ph-$CH_2$—$NH_2$) multi-sheet nanotubes are deposited on the interdigitated electrodes by dielectrophoresis with three drops (8 µL) with respectively a 20 mg/L and a 40 mg/L suspension (FIGS. 8A and 8B).

Figure 9:
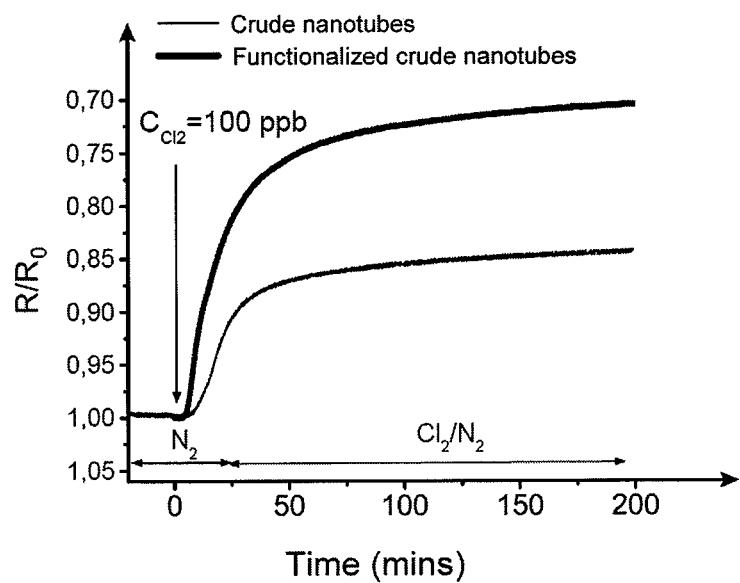
FIG. 9 shows the comparison of the curves for detecting chlorine at a content of 100 ppb (diluted in nitrogen) between the sensors based on «crude» nanotubes and sensors according to the invention based on functionalized nanotubes.

The functionalization leads to a 120% sensitivity gain (at 200 mins) ($S=(R-R_0)/R_0$)*100), toward chlorine diluted in nitrogen at a content of 100 ppb, in sensors compared with sensors based on crude nanotubes without any functionalization (FIG. 9).

Figure 10:
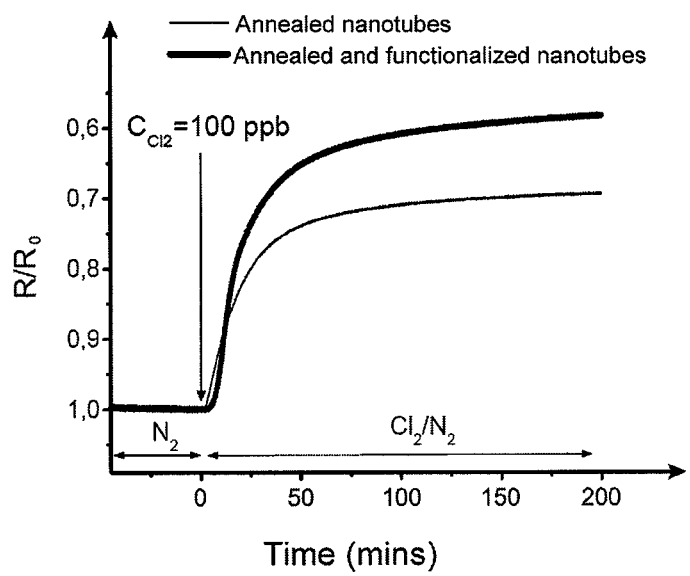
FIG. 10 shows the comparison of the curves for detecting chlorine at a content of 100 ppb (diluted in nitrogen) between the sensors based on annealed nanotubes and the sensors according to the invention based on annealed and functionalized nanotubes.

The functionalization leads to a 35% sensitivity gain (at 200 mins) ($S=(R-R_0)/R_0$)*100), toward chlorine diluted in nitrogen at a content of 100 ppb, in sensors based on «annealed» and functionalized nanotubes compared with sensors based on «annealed» nanotubes without any functionalization (FIG. 10).

Figure 11:
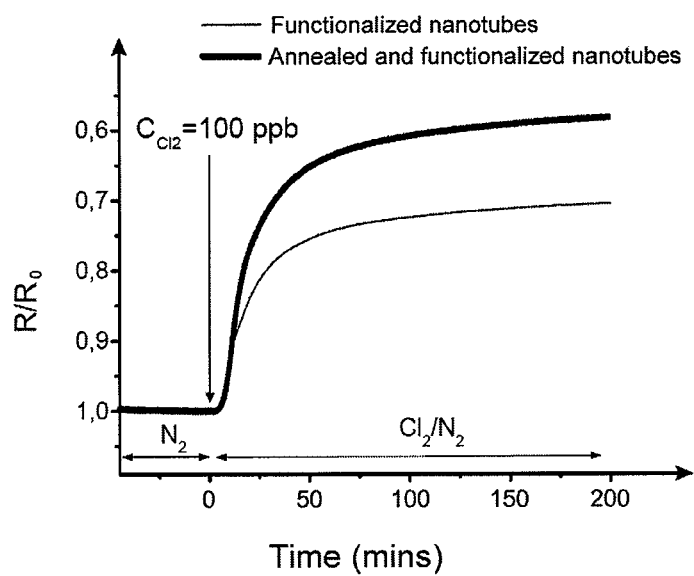
FIG. 11 shows the comparison of the curves for detecting chlorine at a content of 100 ppb (diluted in nitrogen) between the sensors according to the invention either based on functionalized nanotubes, annealed or not.

The sensors based on «annealed» and functionalized nanotubes have a 40% sensitivity gain ($S=(R-R_0)/R_0$)*100) (at 200 mins) toward chlorine diluted in nitrogen at a content of 100 ppb, as compared with sensors based on functionalized nanotubes but not annealed beforehand (FIG. 11).

REFERENCES

[1] Niizeki et al. *Journal of the electrochemical Society* 145 (1998) 2445-2447 "Room temperature operating solid-state sensor for chlorine gas".

[2] Banet et al. *Sensors and transducers* 83 (2007) 1541 "Efficient probes for a fast detection of chlorine gas at ppb level".

[3] Bender et al. *Sensors and actuators B* 77 (2001) 281-286 "Characterization of a $WO_3$ thin film chlorine sensor".

[4] Wei et al. *Sensors and actuators B* 101 (2004) 81-89 "A novel $SnO_2$ gas sensor doped with carbon nanotubes operating at room temperature".

[5] Bittencourt et al. *Sensors and actuators B* 115 (2005) 33 "$WO_3$ films modified with functionalised multi-wall carbon nanotubes: Morphological, compositional and gas response studies".

[6] Patent application US 2007/0145356 (Amlani et al.) published on Jun. 28, 2007.

[7] Kong et al. *Science* 287 (2000) 622 "Nanotube Molecular Wires as Chemical Sensors".

[8] Qi et al. *Nanoletters* 3 (2003) 347 "Toward Large Arrays of Multiplex Functionalized Carbon Nanotube Sensors for Highly Sensitive and Selective Molecular Detection".

[9] Jang et al. *Sensors and actuators B* 99 (2004) 118 "A simple approach in fabricating chemical sensor using laterally grown multi-walled carbon nanotubes".

[10] Valentini et al. *Appl. Phys. Lett.* 82 (2003) 961 "Sensors for sub-ppm $NO_2$ gas detection based on carbon nanotube thin films".

[11] Roy et al. *Vacuum* 77 (2005) 223 "Room temperature sensor based on carbon nanotubes and nanofibres for methane detection".

[12] Li et al. *IEEE Sensors Journal* 6 (2006) 1047-1049 "Nano-Chemical Sensors With Polymer-Coated Carbon Nanotubes".

[13] Wang et al. *Diam. Relat. Mater.* 13 (2004) 1327 "Multi-walled carbon nanotube-based gas sensors for $NH_3$ detection".

[14] Suehiro et al. *Appl. Phys D: Appl. Phys* 36 (2003) 109 "Fabrication of a carbon nanotube-based gas sensor using dielectrophoresis and its application for ammonia detection by impedance spectroscopy".

[15] International application WO 2005/Q26694 (NANOMIX, INC.) published on Mar. 24, 2005.

[16] International application WO 2005/062031 (NANOMIX, INC.) published on Jul. 7, 2005.

[17] Patent application US 2006/0263255 (Amlani et al.) published on Nov. 23, 2006.

[18] U.S. Pat. No. 7,312,095 (NANOMIX, INC.) published on Dec. 25, 2007.

[19] International application WO 2004/000727 (CEA) published on Dec. 31, 2003.

[20] International application WO 2005/033378 (CEA) published on Apr. 14, 2005.

[21] International application WO 2006/097611 (CEA) published on Sep. 21, 2006.

[22] International application WO 2008/078052 (CEA) published on Jul. 3, 2008.

The invention claimed is:

1. A device for detecting at least one chemical compound, the device comprising at least one carbon nanotube with several graphene layers, wherein at least one molecule bearing a group $G_1$ capable of reacting with the chemical compound or a precursor of the group $G_1$ is grafted on the carbon nanotube with several graphene layers, wherein the carbon nanotube with several graphene layers is annealed under an inert atmosphere in a temperature above 1500° C. after being prepared, and before being grafted.

2. The device according to claim 1, wherein the carbon nanotube has a length of between about 1 μm and about 1 mm.

3. The device according to claim 1, wherein the molecule to be grafted is a cleavable aryl salt selected from the group consisting of aryl diazonium salts, aryl ammonium salts, aryl phosphonium salts and aryl sulfonium salts, the aryl group bearing a group $G_1$ capable of reacting with the chemical compound or a precursor of the group $G_1$.

4. The device according to claim 1, wherein the molecule to be grafted is a cleavable aryl salt of the following formula (I):

wherein:
A represents a monovalent anion and
R represents an aryl group R bearing a group $G_1$ capable of reacting with the chemical compound or a precursor of the group $G_1$.

5. The device according to claim 3, wherein the aryl group is selected from the group consisting of aromatic or heteroaromatic carbon structures, consisting of one or more aromatic or heteroaromatic rings each including 3 to 8 atoms, the heteroatom(s) including N, O, P or S.

6. The device according to claim 4, wherein A is selected from the group consisting of halides, haloborates, perchlorates, sulfonates, alcoholates and carboxylates.

7. The device according to claim 1, wherein the molecule grafted on the carbon nanotube is a polymer or copolymer mainly derived from several identical and/or different monomer units, said polymer or copolymer bearing at least one group $G_1$ capable of reacting with said chemical compound or a precursor of the group $G_1$.

8. The device according to claim 7, wherein the monomer units are monomers which are polymerizable via a radical route.

9. The device according to claim 8, wherein the monomers are selected from monomers of the following formula (II):

and wherein the groups $R_1$ to $R_4$, either identical or different, represent a non-metal monovalent atom selected from the group consisting of a halogen atom, a hydrogen atom, a saturated or unsaturated chemical group such as an alkyl, aryl group, a nitrile, a carbonyl, an amine, an amide or a —$COOR_5$ group wherein $R_5$ represents a hydrogen atom or a $C_1$-$C_{12}$, or a $C_1$-$C_6$ alkyl group.

10. The device according to claim 1, wherein the group $G_1$ capable of reacting with the chemical compound is selected from the group consisting of hydroxyl, thiol, azide, epoxide, azyridine, amine, nitrile, isocyanate, thiocyanate, nitro, amide, halide notably alkyl halide, carboxylic acid and ester functions.

11. The device according to claim 1, further comprising a support; and
two electrodes positioned on the support,
wherein the carbon nanotube is configured to ensure electric contact between the two electrodes.

12. The device according to claim 11, wherein the electrodes have an interdigitated comb configuration.

13. The device according to claim 1, wherein the nanotube has an orientation substantially perpendicular with respect to the two electrodes.

14. A system comprising at least two devices according to claim 1.

15. A method of using at least one device according to claim 1 for detecting and optionally quantifying one or more gaseous chemical compounds.

16. The method according to claim 15, wherein the gaseous chemical compound is selected from the group consisting of volatile organic compounds, hydrogen, carbon monoxide, carbon dioxide, chlorine and chlorinated compounds, ammonia, organo-phosphorus gases, hydrocyanic acid, thionyl chloride, phosphene, tetrahydrofurane, methane and dimethyl methyphosphonate.

17. A method for preparing a device for detecting at least one chemical compound according to claim 1, wherein the method comprises depositing on two electrodes, at least one carbon nanotube with several graphene layers, wherein at least one molecule bearing a group $G_1$ capable of reacting with the chemical compound or a precursor of the group $G_1$ is grafted on the carbon nanotube with several graphene layers, and wherein the carbon nanotube ensures electric contact between the electrodes, wherein the carbon nanotube with several graphene layers is annealed in a temperature above 1500° C. in an inert atmosphere after being prepared, and before being grafted.

18. The method according to claim 17, wherein deposition is carried out by dielectrophoresis.

19. The method according to claim 17, wherein the method comprises grafting on the carbon nanotube the molecule bearing a group $G_1$ capable of reacting with the chemical compound or a precursor of the group $G_1$.

20. The method according to claim 17, wherein the method comprises:
- annealing the carbon nanotube with several graphene layers,
- placing the annealed nanotube in contact with a solution $S_2$ containing at least one molecule bearing a group $G_1$ capable of reacting with the chemical compound or a precursor of the group $G_1$ or at least one precursor of the latter to form a mixture;
- submitting the mixture to non-electrochemical conditions so as to graft on the nanotube, the molecule or the precursor;
- recovering the grafted nanotube obtained and depositing the grafted nanotube on two electrodes, notably by dielectrophoresis.

21. The device according to claim 5, wherein the aryl group is mono-substituted or poly-substituted, and wherein the substituent(s) contain one or more hetero-atoms or $C_1$-$C_6$ alkyl groups.

22. The device according to claim 8, wherein the monomer units comprise molecules of the ethylene type.

* * * * *